US009844632B2

(12) United States Patent
Jugl et al.

(10) Patent No.: US 9,844,632 B2
(45) Date of Patent: Dec. 19, 2017

(54) CAP ASSEMBLY FOR A DRUG DELIVERY DEVICE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: SANOFI-AVENTIS DEUTSCHLAND GMBH, Frankfurt an Main (DE)

( * ) Notice: Subject to any disclaimer, the term of this patent is extended or adjusted under 35 U.S.C. 154(b) by 601 days.

(21) Appl. No.: 14/240,802

(22) PCT Filed: Sep. 18, 2012

(86) PCT No.: PCT/EP2012/068293

§ 371 (c)(1),
(2) Date: Feb. 25, 2014

(87) PCT Pub. No.: WO2013/041504

PCT Pub. Date: Mar. 28, 2013

(65) Prior Publication Data

US 2014/0323976 A1 Oct. 30, 2014

(30) Foreign Application Priority Data

Sep. 20, 2011 (EP) .................................... 11181944

(51) Int. Cl.
*A61M 5/32* (2006.01)

(52) U.S. Cl.
CPC ........ *A61M 5/3202* (2013.01); *A61M 5/3213* (2013.01); *A61M 2207/00* (2013.01); *F04C 2270/0421* (2013.01); *Y10T 29/49826* (2015.01)

(58) Field of Classification Search
CPC .............. A61M 5/3202; A61M 5/3204; A61M 5/3213; A61M 2005/3104
See application file for complete search history.

(56) References Cited

U.S. PATENT DOCUMENTS 5,624,402 A * 4/1997 Imbert ................ A61M 5/3134 604/111
6,585,691 B1 * 7/2003 Vitello ................ A61M 5/3134 215/230
2008/0097310 A1 4/2008 Buehler et al.
(Continued)

FOREIGN PATENT DOCUMENTS

EP 0749760 12/1996
JP H08-215307 8/1996
(Continued)

OTHER PUBLICATIONS

International Search Report for Int. App. No. PCT/EP2012/068293, completed Jan. 21, 2013.
International Preliminary Report on Patentability for Int. App No. PCT/EP2012/068293, dated Nov. 6, 2013.

*Primary Examiner* — Kami A Bosworth
(74) *Attorney, Agent, or Firm* — McDonnell Boehnen Hulbert & Berghoff LLP

(57) ABSTRACT

A cap assembly for a drug delivery device is present having a cap body to protect and to receive a distal dispensing end of the drug delivery device, an interlock member operably engaged with the cap body and being further adapted to releasably engage with a distal end section of the device's dispensing end to provide a safety lock for the cap body.

8 Claims, 3 Drawing Sheets

22 24 28 30 33 15 11 34 32 36 13 26 20 20 21 38 14

(56) References Cited

U.S. PATENT DOCUMENTS

| | | | | |
|---|---|---|---|---|
| 2009/0326477 | A1* | 12/2009 | Liversidge | A61M 5/326 604/198 |
| 2010/0234811 | A1* | 9/2010 | Schubert | A61M 5/326 604/198 |
| 2010/0292654 | A1 | 11/2010 | Schraga | |
| 2011/0023281 | A1* | 2/2011 | Schraga | A61M 5/3202 29/426.1 |
| 2011/0077615 | A1 | 3/2011 | Schraga | |
| 2012/0029442 | A1* | 2/2012 | Boyd | A61M 5/3202 604/197 |
| 2012/0191046 | A1* | 7/2012 | Larsen | A61M 5/3202 604/192 |

FOREIGN PATENT DOCUMENTS

| | | | |
|---|---|---|---|
| JP | 2009-538661 | 11/2009 | |
| JP | 2010-540055 | 12/2010 | |
| WO | 02/074369 | 9/2002 | |
| WO | 2007/036676 | 4/2007 | |
| WO | 2008/005315 | 1/2008 | |
| WO | 2009/040603 | 4/2009 | |
| WO | 2009/081103 | 7/2009 | |
| WO | 2009/137486 | 11/2009 | |
| WO | 2010/037828 | 4/2010 | |
| WO | WO 2010/142813 | * 12/2010 | A61M 5/32 |

* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35
```

CAP ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/068293 filed Sep. 18, 2012, which claims priority to European Patent Application No. 11181944.7 filed Sep. 20, 2011. The entire disclosure contents of these applications are herewith incorporated by reference into the present application.

TECHNICAL FIELD

The present invention relates to a cap assembly for a drug delivery device, in particular for a pen-type injector, wherein the cap assembly comprises a supplemental interlock member to provide a safety lock mechanism.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose.

Pen-type injectors but also other drug delivery devices being inter alia adapted to dispense and/or inject a predefined dose of a medicament comprise a dispensing end to be coupled with an injection component, like an injection needle. The dispensing end of the drug delivery which may comprise a cartridge holder therefore features a mechanical coupling to the releasably receive a needle assembly. Typically, the cartridge holder has a threaded socket to threadedly engage with a correspondingly designed needle hub.

In particular with double tipped needle assemblies, the proximal tip of the needle enters the cartridge holder and penetrates a distal seal of a cartridge disposed therein. When not in use, the disposable needle assembly is to be discarded and the cartridge holder section of the drug delivery device is to be protected by a protective cap. Such caps being typically designed to cover the entire cartridge holder comprise an interconnection member to engage with a correspondingly shaped interconnection member of the drug delivery device.

Typically, the releasable interconnection of cap and housing of the drug delivery device comprises some kind of snap-in or clipping feature. Since the drug delivery device is designed and intended for home medication, assembly and disassembly of the cap to and from the housing of the drug delivery device should be easy and should require only minimum pull-off forces. This way, even physically impaired end users or patients are able to put on and to remove the protective cap.

Providing a rather low pull-off or withdrawal force to remove the cap on the one hand enables elderly or mobility impaired persons to remove the cap easily. On the other hand, a cap featuring a low pull-off force may be rather prone to unintentional disassembly. Hence, the cap may automatically and/or unintentionally release. As a consequence, the cartridge holder and the cartridge disposed therein would be no longer protected. Moreover, unintentional release of the cap may also contaminate the cartridge or components of the drug delivery device. In case a needle assembly remains on the distal end of the cartridge holder, unintentional removal of the protective cap may further increase the likelihood of unintentional stitching.

Hence, a rather low pull-off force may be disadvantageous in terms of patient safety. In particular, children or other unauthorized persons may easily remove the cap and may be thereby considerably endangered by the drug delivery device.

One object of the present invention to provide an improved cap assembly for a drug delivery device, which on the one hand is easy to assemble and to disassemble and which, on the other hand can be securely fastened to the drug delivery device. A secure and safe fastening of the cap assembly should increase patient safety. Also, by way of an improved fastening mechanism, unintentional and/or automatic disassembly of cap and drug delivery device should be largely prevented.

SUMMARY

The present invention provides a cap assembly for a drug delivery device having a cap body to protect and to receive a distal dispensing end of the drug delivery device. The cap assembly further comprises an interlock member operably engaged with the cap body and being further adapted to releasably engage with a distal end section of the device's dispensing end. This way, the interlock member provides a safety lock for the cap body and effectively prevents self-acting or automated disassembly of cap body and drug delivery device.

In particular, the cap body may resemble a conventional cap to be mounted on a distal or dispensing end of a drug delivery device. It may be directly coupled and/or fixed with a single or several housing components of the drug delivery device. The interlock member in turn serves as a second fastening means and may engage as well as disengage with a distal end section of e.g. a cartridge holder even when the cap body is in its fastening or mounting position with the drug delivery device. It is particularly intended, that the interlock member provides an additional safety lock mechanism in order to secure the cap body in its mounting or fastening position.

With the interlock member engaged with the distal end section of the device, a disassembly of cap body and drug delivery device is effectively impeded. Disassembly of cap body and device always requires a respective disengaging of interlock member and distal end section of the drug delivery device.

In a preferred embodiment, the cap body comprises a cup-shaped receptacle having at least a first interconnection member at a proximal end thereof to provide a first interconnection with a housing component of the drug delivery device. Hence, the cap assembly can be at least pre-fixed or pre-assembled with the housing of the drug delivery device by way of the first interconnection member provided in or at the cap body. This way, the cap assembly, at least its cap body can be connected to the housing of the drug delivery device irrespective of the configuration of the interlock member.

In a further preferred embodiment, the interlock member comprises a second interconnection member to releasably engage with the distal end section of the device's dispensing end, which may comprise the cartridge holder. This way, the cap assembly can be connected and fixed to the drug delivery device in a two-fold manner. By way of the first interconnection member, the cap body can be attached and fixed to the drug delivery device, thereby providing a rather low pull-off or withdrawal force. By way of the interlock member, the cap assembly can be rigidly fastened with the distal end section of the drug delivery device, thereby providing a safety lock mechanism.

A disassembly of cap assembly and drug delivery device therefore requires first to disengage interlock member and distal end section of the device's dispensing end. Thereafter, conventional and smooth withdrawal of the cap assembly and/or its cap body from the drug delivery device is enabled.

While the first interconnection established between cap body and housing of the drug delivery device only provides a rather low pull-off or withdrawal force, the second interconnection to be established by the interlock member and the distal end section of the device's dispensing end remarkably increases the pull-off force in order to impede unintentional disassembly of cap assembly and drug delivery device. Hence, the pull-off force provided by the second interconnection is substantially larger than the pull-off force provided by the first interconnection.

According to another embodiment, the first and/or second interconnection members comprise an inner thread to engage with an outer thread either provided at the drug delivery device or provided at the distal end section of the device's dispensing end, e.g. its cartridge holder. This way, first and/or second interconnections can be established by way of a threaded engagement of e.g. cap body and housing of the drug delivery device and/or between interlock member and distal end of the device's dispensing end.

Additionally or alternatively it is also conceivable, that the first and/or the second interconnection members comprise at least one radially inwardly extending latch member to establish a positive interlock with a correspondingly shaped radially outwardly protruding catch member. The catch member is either disposed at a distal socket portion of the drug delivery device and/or it is disposed at a proximal portion of the dispensing end of the drug delivery device.

The catch member disposed at a distal socket portion of the drug delivery device is particularly adapted to engage with the interlock member of the cap assembly. In a similar way, a latch member provided at a proximal portion of the dispensing end of the drug delivery device is particularly adapted to engage with the first interconnection member provided at a proximal end of the cup-shaped receptacle of the cap body. Instead of mutually corresponding latch and catch members, the positive interlock can be also provided by way of mutually mating and interengaging snap-fit- or clip-members.

First and second interconnections to be established by mutually corresponding first and second interconnection members of cap body, interlock member and housing of the drug delivery device may both comprise a threaded engagement or a positive-locking. It is also conceivable, that the first interconnection features a positive interlock while the second interconnection is based on a threaded engagement; or vice versa.

According to a further preferred embodiment, the interlock member comprises an inner sleeve extending axially inwardly from a distal end of the cap body. In this embodiment, the second interconnection member is preferably disposed at a proximal portion of said inner sleeve. The inner sleeve and its second interconnection member may be particularly adapted to be screwed onto a threaded socket of a distal end of a cartridge holder component of the drug delivery device.

According to a further embodiment of the cap assembly for a drug delivery device according to the present invention, the cap assembly comprises:

- a cap body being adapted to protect and receive a distal dispensing end of the drug delivery device, and comprising a cup-shaped receptacle having at least a first interconnection member at a proximal end thereof to provide a first interconnection with a housing component of the drug delivery device,
- an interlock member operably engaged with the cap body and comprising a second interconnection member being further adapted to releasably engage with a distal end section of the device's dispensing end to provide a safety lock for the cap body, wherein the interlock member comprises an inner sleeve extending axially inwardly from a distal end of the cap body, with the second interconnection member disposed at a proximal portion of the inner sleeve.

According to a further embodiment, the interlock member and/or its inner sleeve may project from the distal end of the cap body. It may therefore form a distal end thereof. Hence, the cap assembly may comprise two separate components, namely a cap body that serves to protect a cartridge holder of a drug delivery device and an interlock member providing a distal end of the cap but extending in proximal direction inside the cap body with an inner sleeve. The interlock member may protrude from the cap body in distal direction to be gripped by a user and may extend with its inner sleeve in proximal direction inside the cap body.

Depending on the type of first and/or second interconnection, the interlock member, according to a further embodiment, is rotatably supported in the cap body. This is of particular benefit when the cap body is to be clipped onto the housing of the drug delivery device while the second interconnection member of the interlock member is designed to threadedly engage with a correspondingly threaded distal socket of the device's dispensing end. This way, the cap body may remain stationary relative to the housing of the drug delivery device during an engagement and/or disengagement action of interlock member and dispensing end of the drug delivery device.

In a further preferred aspect, the interlock member is also slidably supported in the cap body in axial direction. This way, the interlock member may become subject to an axial displacement when engaged or disengaged with the device's dispensing end.

Moreover and according to a further preferred embodiment, the cap body and the interlock member also comprise mutually corresponding and radially extending stop elements to restrict relative axial displacement of cap body and interlock member. This way, when screwed onto a distal socket of a cartridge holder, the interlock member may exert proximally directed holding forces to the cap body via mutually engaging stop elements. The cap body can therefore be rigidly fixed in axial direction relative to the housing of the drug delivery device.

According to another embodiment, the cap body and the interlock member are integrally formed. They may comprise a single injection molded plastic component to be manufactured in a cost-efficient way, e.g. in a mass-production process.

In still another but independent aspect, the invention also relates to a drug delivery device for injecting a pre-defined dose of a medicament. The drug delivery device comprises a cartridge holder to receive a cartridge filled with a medicament to be dispensed. The device further has a proximal housing component connectable with the cartridge holder and being adapted to accommodate a drive mechanism. The drive mechanism typically comprising at least a piston rod is to be operably engaged with a proximally located piston of the cartridge. This way and by exerting distally directed pressure or thrust to the piston via e.g. the piston rod, a pre-defined amount of the medicament contained in the cartridge can be expelled via a distal dispensing outlet of the cartridge.

The drug delivery device further comprises a cap assembly as described above having a cap body to protect and to receive the cartridge holder of the drug delivery device and further having an interlock member to be operably engaged or fixed with the cap body and being further adapted to releasably engage with a distal end of the cartridge holder.

In a preferred embodiment, the cap body of the cap assembly is adapted to releasably engage with the housing component and/or with a proximal portion of the cartridge holder. Additionally or alternatively, the interlock member is adapted to threadedly engage with a distal socket portion of the cartridge holder being typically adapted and intended to threadedly receive a hub of a needle assembly. This way, a threaded distal socket of the cartridge holder provides a two-fold functionality. On the one hand it provides a mounting base or a releasable needle assembly. On the other hand it provides a mounting base for an interlock member of a cap assembly to provide a safety lock for the cap.

According to another embodiment, the cartridge holder further comprises a radially outwardly extending circumferentially interrupted rim to engage with a radially inwardly extending latch portion of the interlock member. The radially outwardly extending rim provides a catch member and is typically disposed at the distal socket portion at the distal end of the cartridge holder. By having a circumferentially interrupted rim as a catch member, mutual engagement of latch member and catch member may be attained by displacing the cap body and/or the interlock member relative to the cartridge holder in proximal direction e.g. in form of a sliding motion.

For this purpose, mutually corresponding latch- and catch members may comprise slanted or beveled abutment faces, in order to facilitate a snap-in or clipping functionality. Disengagement of the second interconnection may be attained by a rotative displacement of the interlock member or the entire cap assembly relative to the cartridge holder in such a way, that radially inwardly extending latch members of the interlock member flush with a correspondingly shaped recess of the circumferentially interrupted rim. This way, relative axial displacement and a withdrawal of the cap body from the housing of the drug delivery device can be provided.

In still another aspect, a method of releasably interconnecting a cap assembly with a cartridge holder of a drug delivery device is provided. In a first step, the cartridge holder section of the drug delivery device is inserted into a cupped receptacle of a cap body of the cap assembly until a mounting or fastening position has been reached. Thereafter, in a second step, an interlock member operably engaged or connected with the cap body is activated to provide a releasable engagement with a distal end section of the cartridge holder. This way, a safety lock for the cap body relative to the cartridge holder of the drug delivery device can be provided.

In a similar way, also disconnection of cap assembly and drug delivery device can be provided. Here, in an initial step, the interlock member has to be deactivated, e.g. by unscrewing the interlock member from a threaded socket portion of the cartridge holder and/or by disengaging mutually corresponding latch- and catch members. After deactivating the safety lock, the cap body and the entire cap assembly can be withdrawn from the cartridge holder section of the drug delivery device. For the interconnecting as well as for the disconnecting procedure, the cap body may separately engage with the housing of the drug delivery device, e.g. by means of its first interconnection member as described above.

Even though the various embodiments described herein relate to a pen-type injector, the present invention it is by no way limited to this particular kind of drug delivery devices. The cap assembly according to the present invention may be adapted to a plurality and to a large variety of different drug delivery devices, where a dispensing end has to be protected against environmental influences.

Moreover it is to be noted that any features and embodiments of the invention described in connection with the cap assembly equally apply to the mentioned drug delivery device as well as to the method of releasably interconnecting cap assembly and cartridge holder. Mentioning that a component or part is configured or arranged to perform a certain action is also to be understood as a corresponding method step and vice versa.

The term “drug” or “medicament”, as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in the following by making reference to the Figures, in which.

DETAILED DESCRIPTION

Figure 1:
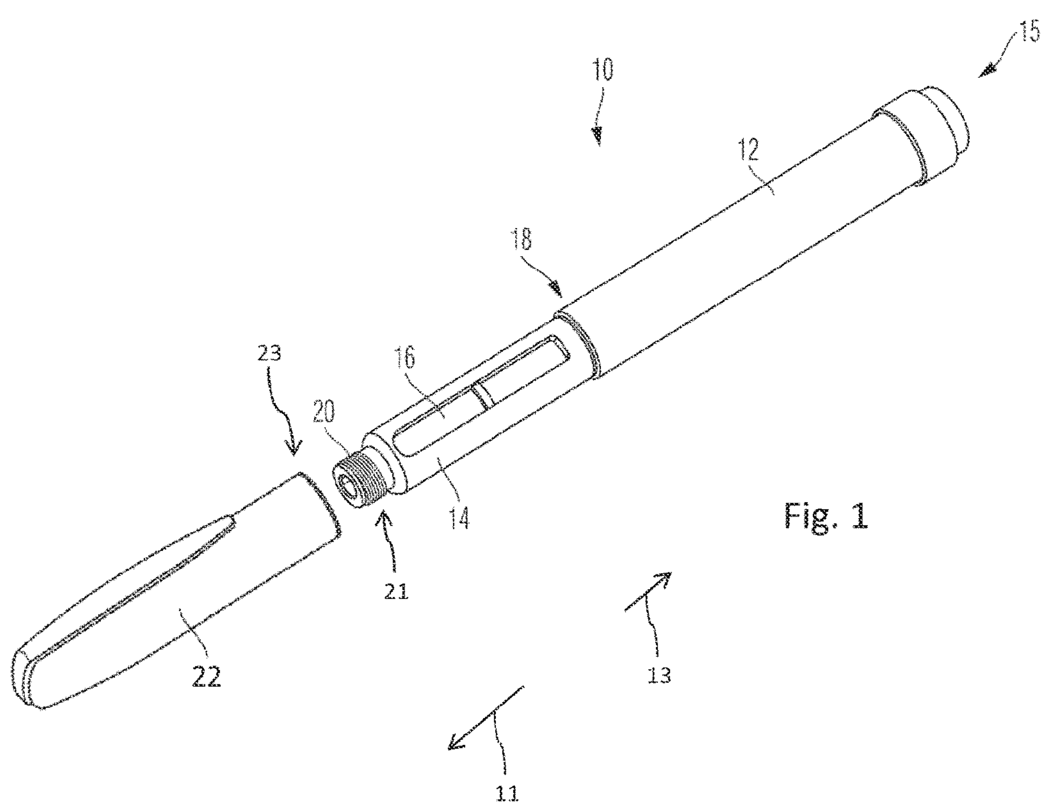
FIG. 1 schematically shows a pen-type injector in a perspective view.

The drug delivery device 10 as schematically illustrated in FIG. 1 comprises a proximal housing component 12 interconnected with a distally arranged cartridge holder 14. Housing 12 and cartridge holder 14 are interconnected with each other and form a stepped down interface 18. Cartridge holder 14 and housing 12 may be threadedly or positively engaged. Depending on the type of drug delivery device 10, which may be either of reusable or disposable type, the interconnection 18 of housing 12 and cartridge holder may be releasable or not.

The cartridge holder 14 serves to accommodate a cartridge being not explicitly illustrated in the present set of Figures. The cartridge holder 14 at least comprises an inspection window 16 allowing to visually inspect the filling level of the cartridge disposed therein. Towards its distal end, the cartridge holder 14, comprises a stepped down socket portion 21 featuring an outer thread 20. Said threaded socket 21 is adapted to threadedly receive a needle hub of a needle assembly, which is also not explicitly shown. If not in use, it is intended, that the cartridge holder 14 is entirely covered with a cap assembly 22 having a cup-shaped receptacle featuring a geometric shape to entirely receive the cartridge holder or the dispensing end section 14 of the drug delivery device 10.

The housing 12 serves to accommodate a drive mechanism which operably engages with a proximally located piston of the cartridge. Operation of the drive mechanism, which is not explicitly shown in the present set of Figures can for instance be controlled and governed by a dose dial and/or dose button 15 provided at a proximal end of the housing 12. According to the present terminology, the distal direction 11 points towards the dispensing end of the drug delivery device 10 and towards the patient, whereas the proximal direction 13 faces away from the dispensing end 14, 20 of the drug delivery device 10 toward the dose dial 15.

The cap assembly 22 typically comprises a first interconnection member 23 at its proximal end in order to engage with a correspondingly designed interconnection member provided at or near the interface 18 of cartridge holder 14 and housing 12. For instance, the cap 22 can be clipped on the cartridge holder 14 and may be fixed thereto by way of the first interconnection member 23, thereby providing a rather low withdrawal force in order to easily withdraw and to smoothly remove the cap assembly 22 prior to use the device 10.

Figure 2:
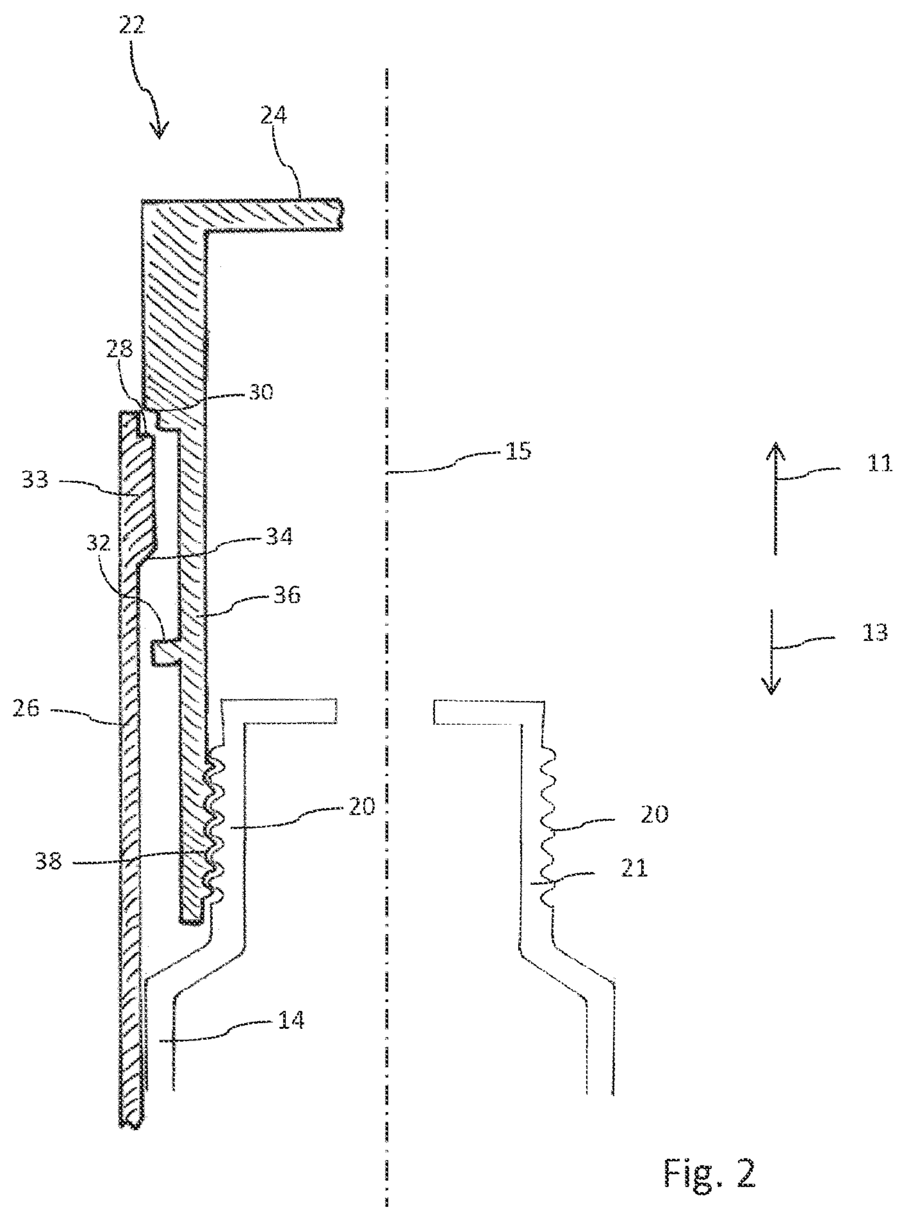
FIG. 2 is illustrative of a first embodiment of the invention and shows a cross section through the distal end of a cartridge holder with a cap assembly mounted thereon.
Figure 3:
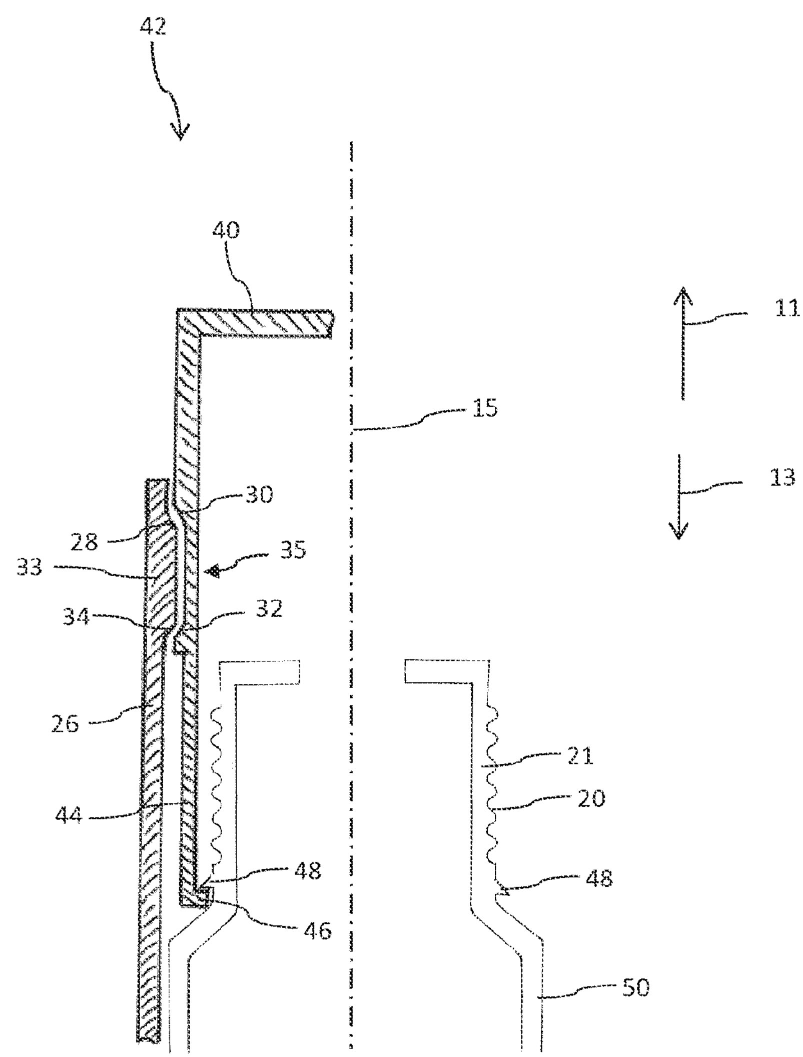
FIG. 3 shows another embodiment of a cap assembly mounted on a cartridge holder.

While the first interconnection of the cap assembly 22 and the housing components 12, 14 of the drug delivery device 10 may comprise a somewhat conventional clipping design, FIGS. 2 and 3 illustrate a second and separate interconnection that provides a safety lock for the cap assembly 22. As shown in the longitudinal cross section according to FIG. 2, the cap assembly 22 comprises two components, namely a cap body 26 and an interlock member 24. While the cap body 26 comprises a cup-shaped receptacle to receive the cartridge holder 14, the interlock member 24 comprises an inner sleeve 36 extending parallel to the cap body 26 in axial direction.

The interlock member 24 is further disposed at a distal end of the cap body 26 and protrudes therefrom. It is rotatably supported by the cap body 26, e.g. it may freely rotate around the longitudinal axis 15 relative to the cap body 26. The inner sleeve 36 of the interlock member 24 comprises an inner thread 38 adapted to threadedly engage with the outer thread 20 of the distal socket 21 of the cartridge holder 14. Additionally, the interlock member 24 can be slidably moved in axial direction relative to the cap body 26 within pre-defined margins. These distal and proximal margins are provided and governed by mutually corresponding and interengaging stop faces 28, 30, 32, 34 provided at the inside wall of the cap body 26 and at the outside wall of the sleeve 36 of the interlock member 24.

The sleeve 36 may be screwed onto the threaded socket 21 of the cartridge holder 14 thereby moving the entire interlock member 24 in proximal direction 13 until a proximally facing stop face 30 of the interlock member 24 abuts against a distally facing stop face 28 of a radially inwardly protruding or thickened portion 33 of the cap body 26. Upon mutual abutment of stop faces 30, 28, the cap body 26 experiences a proximally directed holding force thus impeding a self-acting disassembly of cap assembly 22 and cartridge holder 14. For releasing and disengaging the cap assembly 22, it is required to unscrew the interlock member 24 from the threaded socket portion 21 thereby displacing the interlock member 24 and its inner sleeve 36 in distal direction 11 until the mutually corresponding threads 20, 38 disengage.

As soon as a disengagement configuration has been reached, the cap body 26 is freed to be drawn off from the cartridge holder 14 in distal direction 11. Since cap body 26 and interlock member 24 are arranged in a kind of interleaved or nested configuration, a relative displacement of cap body 26 and interlock member 24 in axial direction 11, 13 is restricted. The distal portion 33 of the cap body 26 is disposed and guided between a distal and a proximal stop face 30, 32 of the interlock member 24 or its inner sleeve 36. Hence, mutual abutment of proximally facing stop face 34 of the cap body 26 with a distally facing abutment face of proximal stop member 32 of the interlock member 34 prevents disengagement of interlock member 24 and cap body 26. Consequently, even when not assembled to the cartridge holder 14, the cap assembly 22 may not disintegrate into its components 24, 26.

Moreover, mutual abutment of stop faces 32, 34 may also support disengaging of the first interconnection of the cap body 26 with the cartridge holder 14 or with the housing 12. This way, unscrewing the interlock member 24 from the distal socket 21 of the cartridge holder 14 may lead to a respective distally directed displacement of the cap body 26 when said stop faces 32, 34 mutually abut, thereby releasing the first interconnection member 23 typically snap-fitted with the interface 18 of cartridge holder 14 and housing component 12.

Instead of a threaded engagement of the inner sleeve 36 and the threaded socket 21, it is also conceivable to provide a positive interlock by means of mutually corresponding snap-fit or clipping elements.

The embodiment according to FIG. 3 relates to a different cap assembly 42 having a cap body 26 being substantially identical to the cap body 26 as described and explained with respect to FIG. 2. In the embodiment according to FIG. 3, the interlock member 40 substantially differs from the embodiment according to FIG. 2 in that its inner sleeve 44 comprises a radially inwardly extending latch member 46 adapted to engage with a radially outwardly extending catch member 48 provided at the proximal portion of the socket portion 21 of the cartridge holder 50. The latch member 46 is preferably disposed at a proximal end of the interlock member 40. It may resemble a radially inwardly but circumferentially interrupted flange portion 46.

This way, a snap-fit or positive lock of interlock member 40 and cartridge holder 50 can be attained. The radially outwardly extending catch members 48 may comprise a circumferentially extending but interrupted rim or may feature a plurality of radially outwardly extending prongs to mate with radially inwardly extending latch members 46 arranged at a proximal end of the inner sleeve 44 of the interlock member 40. Cap body 26 and interlock member 40 may also be freely rotatable with respect to the longitudinal axis 15 as axis of rotation.

The inner sleeve 44 of the interlock member comprises a recess 35 having beveled or slanted stop faces 32, 30 at its proximal and distal margins. The radially thickened portion 33 of the cap body 26 is correspondingly shaped and matches the recess 35 formed in the inner sleeve 44. This way, sleeve 44 and interlock member 40 can be freely rotated relative to the cap body 26 but cap body 26 and interlock member 40 remain axially fixed. Hence, the interlock member automatically engages with the radially outwardly extending prongs 48 when the cap assembly 42 is mounted on the cartridge holder 14. The first and second interconnections between cap body 26 and housing 12, 14 as well as between interlock member 40 and cartridge holder 50 can be almost simultaneously established. As illustrated in FIG. 3, mutual engagement of prongs or rim 48 and latch members 46 effectively prevent self-acting release of the interlock member 40 from the cartridge holder 50 and thereby serves as a safety lock for the cap body 26.

Disengagement of interlock member 40 can be attained by rotating the interlock member 40 relative to the cartridge holder 50, until the radially inwardly extending latch members 46 flush in axial direction 11, 13, with a correspondingly shaped interruption of the prongs 48 or of the circumferentially extending rim 48. Then, interlock member 40 and cap body 26 can be displaced in distal direction relative to the cartridge holder 50.

Even though the embodiment according to FIG. 3 illustrates two separate components, namely cap body 26 and interlock member 40, such a cap assembly 42 may also be designed by a single component, wherein cap body 26 and interlock member 40 are integrally formed. Then, a rotative disengaging motion of the interlock member 40 also comes along with a corresponding rotative movement of the cap body 26.

The invention claimed is:

1. A cap assembly for a drug delivery device, the cap assembly comprising:

a cap body to protect and to receive a distal dispensing end of the drug delivery device, and comprising a receptacle having at least a first interconnection member at a proximal end thereof to releasably engage with a housing component of the drug delivery device, an interlock member operably engaged with the cap body and comprising a second interconnection member to releasably engage with a distal end section of the distal dispensing end to provide a safety lock for the cap body, wherein engagement of the second interconnection member with the distal end section of the distal dispensing end prevents an engagement of the first interconnection member with the housing component of the drug delivery device from being released, wherein the interlock member comprises an inner sleeve extending axially inwardly in a proximal direction from a distal end of the cap body, with the second interconnection member disposed at a proximal portion of the inner sleeve, wherein a portion of the interlock member protrudes in a distal direction from the distal end of the cap body, wherein the second interconnection member is threadedly engageable with the distal end section or wherein the second interconnection member is interlockable with the distal end section by way of a snap-fit engagement, wherein the cap body and the interlock member comprise at least a first pair of mutually corresponding and radially extending stop elements to restrict relative axial displacement of the cap body with respect to the interlock member and to allow the interlock member to exert proximally directed holding forces to the cap body via the stop elements.

2. The cap assembly according to claim 1, wherein the first or second interconnection member comprises an inner thread to engage with an outer thread of the drug delivery device.

3. The cap assembly according to claim 1, wherein the interlock member forms a distal end of the cap assembly.

4. The cap assembly according to claim 1, wherein the interlock member is rotatably supported in the cap body.

5. The cap assembly according to claim 1, wherein the interlock member is slidably supported in the cap body in an axial direction.

6. A drug delivery device for injecting a predefined dose of a medicament, comprising:

a distal dispensing end to receive a cartridge filled with a medicament to be dispensed, a housing component located proximal to and connectable with the distal dispensing end adapted to accommodate a drive mechanism to operably engage with a proximally located piston of the cartridge, and a cap assembly according to claim 1.

7. A method of releasably interconnecting a cap assembly according to claim 1 with a distal dispensing end of a drug delivery device, comprising the steps of:

inserting the distal dispensing end of the drug delivery device into the receptacle of the cap body until a mounting position has been reached, activating the interlock member operably engaged with the cap body to releasably engage with the distal end section of the distal dispensing end for providing a safety lock for the cap body.

8. The cap assembly according to claim 1, wherein release of the engagement of the second interconnection member with the distal end section of the distal dispensing end leads to a distally directed displacement of the cap body when said first pair of mutually corresponding and radially extending stop elements mutually abut, thereby releasing the engagement of the first interconnection member with the housing component of the drug delivery device.

* * * * *